United States Patent [19]
Pozzi et al.

[11] Patent Number: 5,519,322
[45] Date of Patent: May 21, 1996

[54] MAGNETIC FIELD METHOD AND APPARATUS FOR EVALUATING IN SITU AND/OR MEASURING THE PREMEABILITY OF A ROCK FORMATION

[75] Inventors: Jean-Pierre Pozzi, Meudon; Jean-Pierre Martin, La Garenne Colombes, both of France

[73] Assignee: Compagnie Generale de Geophysique, Massy, France

[21] Appl. No.: 392,328

[22] Filed: Feb. 22, 1995

[30] Foreign Application Priority Data

Feb. 22, 1994 [FR] France .................... 94 01965

[51] Int. Cl.⁶ .............. G01V 3/18; G01V 3/26
[52] U.S. Cl. ............ 324/346; 166/250.02; 324/353
[58] Field of Search .................. 324/303, 323, 324/340, 344, 345, 346, 351, 353, 377; 73/152; 166/250.01, 250.02, 252.5, 66

[56] References Cited

U.S. PATENT DOCUMENTS

| | | | |
|---|---|---|---|
| 3,116,449 | 12/1963 | Vogel | 324/355 X |
| 3,621,380 | 11/1971 | Barlow, Jr. | 324/345 |
| 4,427,944 | 1/1984 | Chandler | 324/353 |
| 5,151,658 | 9/1992 | Muramatsu et al. | 324/346 |
| 5,417,104 | 5/1995 | Wong | 324/353 X |

Primary Examiner—Gerard R. Strecker
Attorney, Agent, or Firm—Sughrue, Mion, Zinn, Macpeak & Seas

[57] ABSTRACT

A method and the apparatus for in situ analysis of a rock formation that already contains fluid in its interstices an excitation device is provided for imparting motion to the fluid relative to the rock formation and the magnetic fields created by the relative motion of the fluid in the rock formation measured. The permeability of the rock formation are deduced from the measurement. The measurement system is particularly applicable to in situ measurement of the permeability of rocks, e.g. down an oil well.

13 Claims, 1 Drawing Sheet

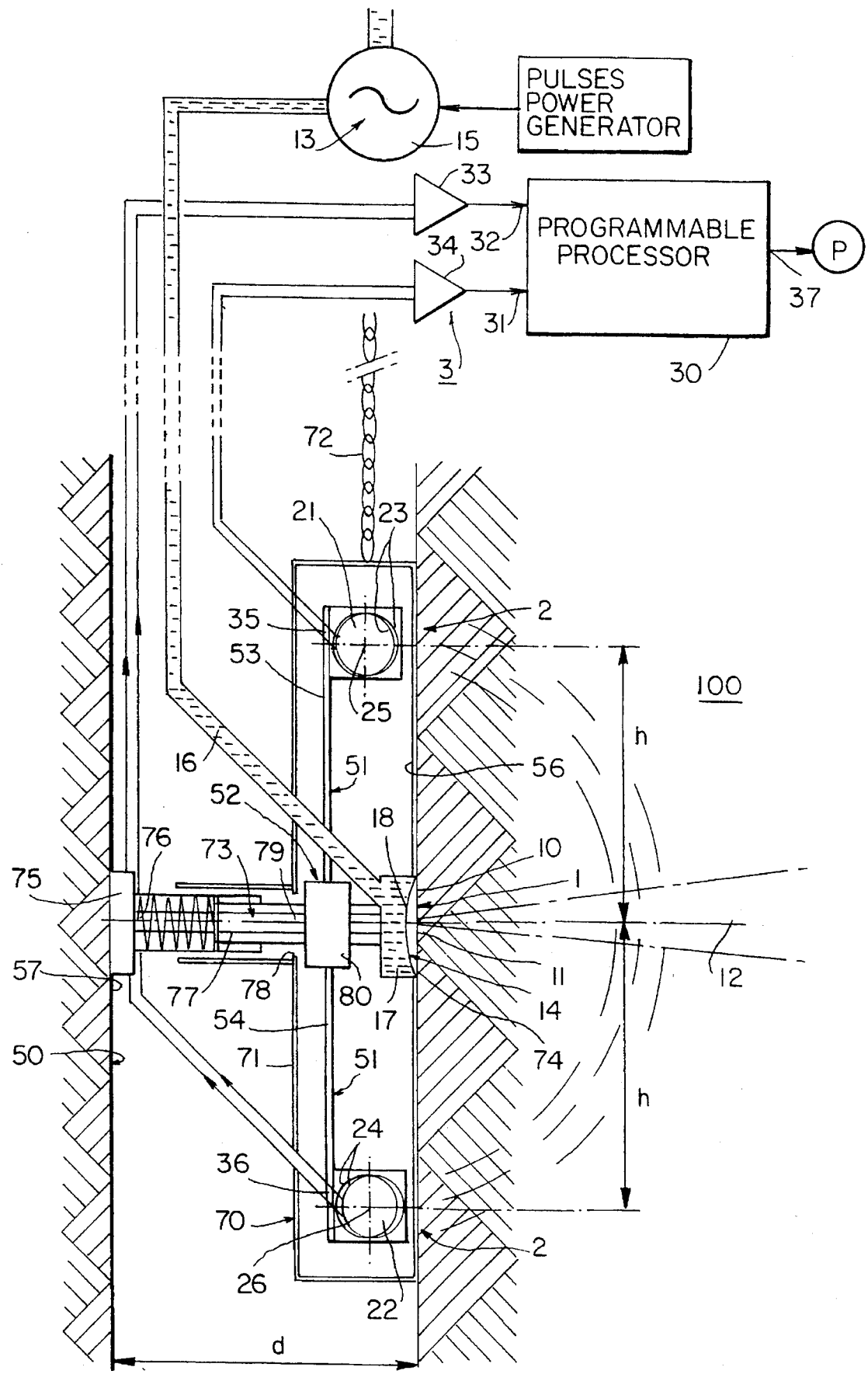

MAGNETIC FIELD METHOD AND APPARATUS FOR EVALUATING IN SITU AND/OR MEASURING THE PREMEABILITY OF A ROCK FORMATION

The present invention relates to a method and apparatus enabling the permeability of a rock formation to be evaluated. It is particularly advantageously applied to an in situ determination of the permeability of a geological formation, e.g. surrounding an oil well.

BACKGROUND OF THE INVENTION

It is known that oil is extracted from wells drilled in oil fields which are to be found in numerous types of ground and subsoils that do not all have the same production quality. This quality depends essentially on the quantity of oil that is not only available but also recoverable, and therefore it depends particularly, but not exclusively, on the permeability of the rock formation in which it is imprisoned, i.e. the ease with which the oil can flow to the well for subsequent extraction therefrom by techniques that are well known in themselves.

It will therefore be understood that it is important to know or to evaluate the permeability of any geological formation in which a fluid deposit might be worked, e.g. a deposit of oil or of natural gas.

One of the first known methods of evaluating the permeability of a rock formation consists in extracting cores of the formation and then in analyzing the cores in a laboratory. That method presents numerous drawbacks, in particular the fact that it is very difficult to deduce the real value of the permeability of the rock formation on the basis of measurements performed in a laboratory.

To mitigate that drawback, attempts have been made to implement methods and to provide apparatuses intended to measure the permeability of a rock formation in situ. The document constituted by U.S. Pat. No. 4,427,944 discloses a method and apparatus enabling the permeability of a rock formation to be evaluated in situ, e.g. down an oil well. The method described in that document consists in position an excitation source in contact with the side wall of the well and substantially at a point situated at the level where the permeability is to be measured, in controlling said source so as to cause it to produce a transient electrokinetic potential in the rock formation around the point of contact, in measuring the amplitude of said electrokinetic potential, in providing a characteristic signal that is a function of the response time of said electrokinetic potential created in the rock formation, and in determining the permeability of said rock formation around the point of contact as a function of the characteristic signal.

The apparatus that enables that method to be implemented is essentially constituted by a tool capable of setting up a transient electro-kinetic potential in the rock formation, means for positioning the tool in contact with the wall of the well substantially at a point level with the rock formation where it is desired to measure permeability, means for controlling the tool to cause it to produce excitation capable of actually delivering the transient electrokinetic potential, at least two electrodes which are pressed against the wall of the well on either side of the excitation point to measure the electrokinetic potential, and means for processing the signal delivered by said electrodes in order to determine the permeability of the rock formation at the excitation point.

That method and apparatus have the advantage of enabling the permeability of geological formations to be measured in situ in a well formed through such geological formations, however they nevertheless present the following drawbacks. The electro-kinetic potential to be detected is always very small, whereas it is Generally embedded in spontaneous potential background noise that is quite large. Contact between the electrodes and the wall of the well must be constant and excellent, and that is very difficult to achieve given the shape of a borehole, and the presence of mud in the well can set up interfering impedances between the electrodes and the wall. Consequently, even when theoretically possible, the measurement of electro-kinetic potential is not reliable and the results osf tests as provided by the means for processing the signals delivered by the electrodes are falsified.

OBJECTS AND SUMMARY OF THE INVENTION

An object of the present invention is thus to implement a method for in situ evaluation of the permeability of a rock formation, and to provide apparatus for implementing the method. This method and apparatus mitigate the drawbacks mentioned above to a considerable extent.

More precisely, the present invention provides a method of evaluating the permeability of a rock formation, consisting:

in filling any interstices present in said rock formation with a given interstitial fluid;

in imparting motion to said interstitial fluid relative to said rock formation;

in measuring the magnetic field produced by the relative motion of said interstitial fluid in the rock formation; and in determining the permeability of said rock formation as a function of said measured magnetic field.

The invention also provides an apparatus for evaluating the permeability of a rock formation containing an interstitial fluid in its interstices, the apparatus comprising:

means for imparting motion to said interstitial fluid relative to said rock formation;

means for measuring the magnetic fields produced by the relative motion of said interstitial fluid in the rock formation; and means for determining the permeability of said rock formation as a function of the measured value of said magnetic field.

BRIEF DESCRIPTION OF THE DRAWING

Other characteristics and advantages of the present invention appear from the following description given with reference to the accompanying drawing which is purely illustrative and non-limiting, and in which:

The sole FIGURE is a diagram showing one embodiment of apparatus of the invention enabling the permeability of a rock formation to be evaluated in situ, in an application to a well in a deposit of oil or of natural gas.

MORE DETAILED DESCRIPTION

The present invention relates to a method of evaluating the permeability of a rock formation 100, e.g. a geological formation in which an oil well or the like 50 has been made.

The method consists firstly in filling the interstices that might be present in the rock formation, if they are not already filled naturally, with a given fluid, e.g. air or any other fluid that is commonly used in oil wells.

When the interstices of the rock formation are filled with such a fluid, motion is imparted to said interstitial fluid relative to the rock formation 100 by any of the means described below, essentially by pulse generating means. When the interstitial fluid is set into motion, electrical currents flow and the flow of those currents creates a magnetic field. The method of the invention then consists in measuring the magnetic field induced in the rock formation by the motion of the interstitial fluid relative to the rocks of the geological formation under test.

To facilitate evaluation of permeability, the value of the measured magnetic field is preferably converted into another magnitude that is proportional thereto, e.g. into an electrical signal that is easier to process by various means such as memories, computers, etc.

In the final step of the method, the permeability of the rock formation is evaluated as a function of the measured magnetic field, e.g. by means of charts or by using a computer programmed on the basis of such charts which are then essentially constituted by banks of data.

The banks of data are generated for example on the basis of experiments that consist in applying the method of the invention to samples of rock whose permeability has been measured by known earlier methods. The experiments thus establish correspondence between the values of the induced magnetic field as measured and the known permeability values, and the results are stored in memories for the banks of data.

When it is desired to evaluate the still-unknown permeability of a rock formation, it suffices to measure the magnetic field induced in the rock formation by implementing the method of the invention as described above, and to interrogate the banks of data which provide an output signal constituting the permeability value that corresponds to the measured value of the induced magnetic field, the permeability value being obtained directly or by extrapolation from the stored permeability values.

The method described above thus makes it possible to evaluate the permeability of a rock formation in the vicinity of the point at which the interstitial fluid has been set into motion. To evaluate the permeability of the rock formation overall, e.g. along a well made through the rock formation, the method of the invention is applied a plurality of times along the well.

Nevertheless, under such circumstances, it is not necessary to interrogate the above-mentioned banks of data after measuring the induced magnetic field at each point along the well. It suffices to know the value of the permeability at a single point and thereafter, at other points along the well, merely to measure the value of the induced magnetic field, since experience has shown that the value of the permeability of a rock formation is proportional to the measured value of the induced magnetic field. Similarly, if it is sufficient merely to know the variation in the permeability of the rock formation in the vicinity of the well, then it will suffice to measure the variation in the induced magnetic field as measured along the well.

It can also happen that at the location where it is desired to determine the permeability of a geological formation, there exists a secondary magnetic field considered as constituting interference relative to the magnetic field induced by the relative displacement of the interstitial fluid. Under such circumstances, the method consists in measuring the value of the interfering magnetic field and the value of the total magnetic field at the measurement location while the interstitial fluid is being excited, and then in obtaining the value of the induced magnetic field by subtracting the value of the interfering magnetic field from that of the total magnetic field.

The invention also provides apparatus enabling the above-described method to be implemented, with the sole figure showing an embodiment of the apparatus in its application to measuring the permeability of the rock formation 100. To simplify the description, the interstices of the formation are assumed to be already filled with the interstitial fluid mentioned in the description of the method.

The apparatus includes means 1 for imparting motion to the interstitial fluid relative to the rock formation 100, means 2 for measuring the magnetic field created by the flow in the rock formation of the electrical currents produced by said relative motion of the interstitial fluid, and means 3 for determining the permeability of the rock formation as a function of the measured value of the induced magnetic field.

The means 1 for imparting motion to the interstitial fluid relative to the rock formation 100 may be constituted in various different ways. In a preferred embodiment, they may be constituted by means 10 effective at substantially a point 11 of the rock formation, and more particularly of the wall 56 of the well 50 to provide excitation along a given direction 12 substantially perpendicular to said wall 56 and directed into the rock formation.

In one possible embodiment, these means 10 for exciting the interstitial fluid are constituted by injection means 13 for injecting an auxiliary fluid under pressure such as water or the like, which comprises a pump 15 which is controlled, e.g. cyclically at a given relatively low frequency, to send pulses of the auxiliary fluid into a duct 16 that opens out at the point 11, thereby injecting the fluid into the rock formation and as a result giving rise to the above-described relative displacement of the interstitial fluid.

In another embodiment, the means 10 may be constituted by means 14 for delivering compression waves and comprising a pressure chamber 17 separated from the wall 56 of the well 50 substantially at the excitation point 11 by a flexible and resilient membrane 18 and, for example, the same pump 15 as described above which applies the same pulses of auxiliary fluid under pressure, but into the chamber 17. It is then the pressure created at the membrane 18 that transmits the pulses. This embodiment has the advantage of keeping the auxiliary fluid separate from the interstitial fluid and makes it possible to perform measurements dynamically.

Whatever the embodiment of the means 10 for causing the interstitial fluid to move relative to the rock formation, it is advantageous for the means 2 for measuring the induced magnetic field as produced by the relative movement of the fluid in the rock formation to be constituted by at least one magnetometer.

In the example shown in the sole figure, the apparatus includes two magnetometers represented diagrammatically by two magnetic coils 21 and 22 disposed substantially symmetrically about a plane passing through the point 11, containing the direction 12, and substantially perpendicular to the wall 56. Advantageously, the turns 23 and 24 of the two coils are wound in the same direction relative to a common reference so that the measurement of the magnetic field is as accurate as possible.

Nevertheless, it must be understood that this configuration is not to be considered as constituting a limitation on the manner in which the magnetic coil means 2 are implemented.

In an embodiment more specifically adapted to in situ measurement of the permeability of the rock formation 100 through which there passes a borehole 50 having a diameter whose value is designated "d", the apparatus further includes controllable means 51, controllable telescopic arms or the like 53, 54 for holding the two coils 21, 22 at a given distance "h" from the above-defined point 11. These means also enable the two coils to be held a certain distance from the wall 56 of the well 50, thereby avoiding any need for them to be in contact with said wall.

It should be observed that the Applicants have discovered that the signals delivered by the coils have a maximum amplitude when "h" is substantially equal to nine-tenths of "d" (h≈0.9×d), and the axes 25 and 26 of the two coils 21 and 22 are substantially parallel to each other and perpendicular to the direction 12.

In a preferred embodiment of the apparatus, the means 3 for determining the permeability of the rock formation 100 at the excitation point 11 as a function of the measured magnetic field comprises a programmable processor unit 30 including at least two signal inputs 31 and 32, and first and second means 33 and 34 such as differential amplifiers for applying the signals obtained at the outputs 35 and 36 of the two coils 21 and 22 to the two inputs 31 and 32 respectively of the processor unit 30.

When there exists a secondary magnetic field, such as the earth's magnetic field and/or the remanent magnetic field of the rocks at the excitation point 11, which field is considered as an interfering field relative to the magnetic field induced by the relative motion of the interstitial fluid, then the above-defined means 2 for measuring the value of the magnetic field include means for measuring the value of the secondary magnetic field, means for measuring the value of the total magnetic field that exists at the point 11 during excitation of the interstitial fluid, and means for subtracting the value of the secondary magnetic field from that of the total magnetic field.

The means for measuring the value of the secondary magnetic field may be of any type depending on the nature of the field, and they are mounted to co-operate with the means 3 so that the values they deliver are continuously subtracted from those delivered by the means 2. When the value of the secondary magnetic field is known, it may be stored in the processor unit 30 and subtracted directly from the value delivered at the output of the measurement means 2.

The processor unit 30 is advantageously constituted, for example, by a microcomputer or the like programmed to deliver at its output 37 a value that is representative of the measured permeability. The program of the unit can be based on charts that have been determined for example by experiment.

In the advantageous application of the apparatus of the invention to measuring the permeability of the rock formation around a borehole as illustrated in the sole figure, the apparatus includes a tool 70 constituted, for example, by an enclosure 71 made of a material that is preferably insulating, and that is suitable for being lowered down the well by any appropriate means, in particular by a cable 72 associated with a winch or the like situated at the surface of the ground in which the well is made.

This enclosure houses all of the means required at the point 11 for implementing the excitation in a given direction 12 that is substantially perpendicular to the wall 56 of the well. The said means being constituted by: the end of the duct 16 of the chamber 17 with the membrane 18 that is open to the side of the enclosure 71 through a window 74 made in the wall of said enclosure; the means 2 for measuring the magnetic field, and in particular the two magnetic coils 21 and 22; and the controllable means 51, e.g. the controllable telescopic arms or the like 53 and 54 for holding the two coils 21 and 22 at a given distance "h" from the point 11.

The enclosure 71 also encloses means 52 for controlling the controllable means 51, together with means 73 enabling the enclosure to be pressed against the wall 56 in such a manner as to be capable of achieving optimum excitation of the interstitial fluid.

In an advantageous embodiment, the means 73 which enable the enclosure to be positioned in the well so that its window 74 is pressed against the wall 56 comprise, in outline, a pad 75 mounted at the end 76 of a telescopic arm 77 that passes through the wall of the enclosure 71 via an opening 78. The other end 79 of the telescopic arm is, for example, mounted in association with a controllable gear box 80 or the like that is secured to the enclosure 71. The telescopic arm 77 extends along substantially the same direction as the above-defined excitation direction 12, and the opening 78 is substantially opposite to the window 74 that surrounds the excitation point 11.

In this way, when the enclosure is lowered to a given point in a well and when it is designed to perform a permeability measurement substantially at that point, the gear box 80 is driven, e.g. by means of an electric motor, to extend the telescopic arm 77 until the pad 75 comes into abutment against the portion 57 of the wall of the well that is opposite the portion of its wall on which the location of the excitation point 11 is defined. By pressing against said wall portion 57, the pad exerts a reaction force which enables the window 74 to be pressed firmly against the wall 56 around the excitation point 11. The tool is then properly positioned and the permeability measurement can be performed.

When the means 73 are made as described above, the means 52 for controlling the controllable means 51 may advantageously be coupled with said means 73, essentially via the gear box 80.

Under such circumstances, the gear box then has a respective outlet for each of the three telescopic arms 53, 54, and 77 which may be of the rack-and-pinion type. In an application to measuring the permeability of a rock formation around a borehole, the gear box is designed in such a manner that an extension of the telescopic arm 77 through a first given value "$\Delta d$" there corresponds an extension through a value equal to "$0.9 \times \Delta d$" of the two telescopic arms 53 and 54. The distance separating each of the two magnetic coils 21 and 22 from the excitation point 11 is thus automatically related to the diameter of the well at the excitation point 11.

Naturally, the embodiment of the means essentially constituted by the telescopic arms 53, 54, and 77 and the gear box 80 as described above is given purely by way of example and the person skilled in the art and aware of the functions of said means could easily find other embodiments.

The Applicants have found that measurements performed by means of the method and the apparatus as described above are more representative of the permeability of the volume of rock subjected to the excitation source than are measurements obtained using prior art methods and apparatuses, and are therefore much more reliable.

We claim:

1. A method of evaluating the permeability of a rock formation, the steps of:

filling any interstices present in said rock formation with a given interstitial fluid;

imparting motion to said interstitial fluid relative to said rock formation when the interstices present in said rock are filled with said interstitial fluid;

measuring the magnetic field produced by the relative motion of said interstitial fluid in the rock formation; and determining the permeability of said rock formation as a function of said measured magnetic field.

2. A method according to claim 1, wherein, when a secondary magnetic field is present in the rock formation, the method consists in measuring the value of the secondary magnetic field, in measuring the value of the total magnetic field when the interstitial fluid is set into motion relative to the rock formation, and in subtracting the value of the secondary magnetic field from the value of the total magnetic field.

3. Apparatus for evaluating the permeability of a rock formation containing and interstitial fluid in its interstices, the apparatus comprising:

means for imparting motion to said interstitial fluid relative to said rock formation, said motion of said interstitial fluid creating an electric current;

means for measuring the magnetic fields produced by the electric current created by the relative motion of said interstitial fluid in the rock formation; and means for determining the permeability of said rock formation as a function of the measured value of said magnetic field.

4. Apparatus according to claim 3, wherein the means for imparting motion to said interstitial fluid relative to said rock formation are constituted by means effective substantially at a point of said rock formation for performing excitation in a given direction, and that the means for measuring the magnetic field produced by the relative motion of the interstitial fluid in the rock formation are constituted by at least one magnetic coil.

5. Apparatus according to claim 4, including at least two magnetic coils disposed substantially symmetrically about a plane passing through said excitation point and containing said direction, the two magnetic coils having turns that are wound in the same direction relative to a common reference.

6. Apparatus according to claim 5, wherein, when the permeability of the rock formation is measured in a borehole of given diameter, the apparatus includes controllable means for holding the two said coils at a given distance from said point, which distance is a function of the diameter of said well.

7. Apparatus according to claim 6, including means for controlling the controllable means for holding said two coils in such a manner that the distance separating each coil from said point is substantially equal to nine-tenths of the diameter of said well.

8. Apparatus according to claim 5, wherein the axes of the coils are substantially parallel to each other and perpendicular to said direction.

9. Apparatus according to claim 4, wherein the means effective substantially at a point of said rock formation for performing excitation in a given direction are constituted by means for injecting an auxiliary fluid under pressure.

10. Apparatus according to claim 4, wherein the means effective substantially at a point of said rock formation for performing excitation in a given direction are constituted by means for emitting compression waves.

11. Apparatus according to claim 3, wherein the means for determining the permeability of said rock formation as a function of the measured value of said magnetic field comprise a programmable processor unit including at least one signal input and means for applying the signals applied at the output of said coil to the input of said processor unit.

12. Apparatus according to claim 3, wherein the means for measuring the magnetic field produced by the relative motion of said interstitial fluid in the rock formation are constituted by at least one of the following means: a magnetometer, a magnetic coil.

13. Apparatus according to claim 3, wherein, when a secondary magnetic field is present in the rock formation, the means for measuring the value of the magnetic field produced by the relative motion of said interstitial fluid in the rock formation include means for measuring the value of the secondary magnetic field, means for measuring the value of the total magnetic field, and means for subtracting the value of the secondary magnetic field from the value of the total magnetic field.

* * * * *